United States Patent
Orge (10) Patent No.: US 11,980,574 B2
(45) Date of Patent: May 14, 2024

(54) OCULAR DEVICE FOR TREATING GLAUCOMA AND RELATED MINIMALLY INVASIVE GLAUCOMA SURGERY METHOD

(71) Applicant: UNIVERSITY HOSPITALS HEALTH SYSTEM, INC., Cleveland, OH (US)

(72) Inventor: Faruk Orge, Cleveland, OH (US)

(73) Assignee: UNIVERSITY HOSPITALS HEALTH SYSTEM, INC., Cleveland, OH (US)

( * ) Notice: Subject to any disclaimer, the term of this patent is extended or adjusted under 35 U.S.C. 154(b) by 758 days.

(21) Appl. No.: 17/269,430

(22) PCT Filed: Aug. 19, 2019

(86) PCT No.: PCT/US2019/046999
§ 371 (c)(1),
(2) Date: Feb. 18, 2021

(87) PCT Pub. No.: WO2020/050968
PCT Pub. Date: Mar. 12, 2020

(65) Prior Publication Data
US 2021/0177657 A1    Jun. 17, 2021

Related U.S. Application Data

(60) Provisional application No. 62/726,482, filed on Sep. 4, 2018.

(51) Int. Cl.
*A61F 9/007* (2006.01)
(52) U.S. Cl.
CPC .. *A61F 9/00781* (2013.01); *A61F 2220/0016* (2013.01)

(58) Field of Classification Search
CPC ........ A61F 9/00781; A61F 9/007; A61F 9/00; A61F 2220/0008; A61F 2220/0016;
(Continued)

(56) References Cited

U.S. PATENT DOCUMENTS 6,626,858 B2    9/2003    Lynch et al.
6,962,573 B1    11/2005   Wilcox
(Continued)

FOREIGN PATENT DOCUMENTS

WO    2016/023942 A1    2/2016

OTHER PUBLICATIONS

Extended European Search Report corresponding to European Patent Application No. 19857483.2 dated, May 10, 2022.
(Continued)

*Primary Examiner* — Benjamin J Klein
*Assistant Examiner* — Gabriella E Burnette
(74) *Attorney, Agent, or Firm* — Renner, Otto, Boisselle & Sklar, LLP (57) ABSTRACT

A bypass device can be implanted into a body tissue to provide fluid channels through the body tissue. The bypass device includes an open tubular base, and a plurality of pronged features attached to the open tubular base, the pronged features being reconfigurable from a first position to a second position. In the first position the pronged features extend longitudinally along a plane of the open tubular base, and the pronged features are reconfigurable to the second position by flexing the pronged features relative to the tubular base, such that in the second position the pronged features are configured for insertion through the body tissue. The pronged features may be configured as opposing arrow-shaped tangs that are flexed to form tent structures that are insertable through the body tissue. The bypass device may be used in a minimally invasive glaucoma surgery (MIGS)
(Continued)

for treating glaucoma to define fluid flow channels that permit aqueous humor to pass through the trabecular meshwork and into Schlemm's canal.

13 Claims, 7 Drawing Sheets

(58) Field of Classification Search
CPC .. A61F 2220/00025; A61F 2009/00891; A61F 2/15; A61F 2250/0013; A61M 27/00
See application file for complete search history.

(56) References Cited

U.S. PATENT DOCUMENTS

| | | | |
|---|---|---|---|
| 8,771,216 | B2 | 7/2014 | Orge |
| 9,827,143 | B2 | 11/2017 | Lynch et al. |
| 2002/0143284 | A1 | 10/2002 | Tu et al. |
| 2008/0288082 | A1* | 11/2008 | Deal ................. A61M 27/008 623/23.7 |
| 2009/0082863 | A1* | 3/2009 | Schieber ............... A61F 9/0017 623/6.13 |
| 2009/0204053 | A1 | 8/2009 | Nissan et al. |
| 2011/0196487 | A1* | 8/2011 | Badawi ..................... A61F 2/88 623/4.1 |
| 2014/0081195 | A1* | 3/2014 | Clauson .............. A61F 9/00781 604/8 |
| 2014/0303544 | A1 | 10/2014 | Haffner et al. |
| 2015/0250649 | A1 | 9/2015 | Euteneuer et al. |
| 2016/0067093 | A1 | 3/2016 | Johnson et al. |
| 2016/0302965 | A1 | 10/2016 | Erickson et al. |
| 2018/0125710 | A1 | 5/2018 | Schachar et al. |
| 2018/0133150 | A1 | 5/2018 | de Juan, Jr. et al. |

OTHER PUBLICATIONS

International Search Report and Written Opinion for corresponding International Patent Application No. PCT/US2019/046999 mailed on Nov. 7, 2019.

* cited by examiner

OCULAR DEVICE FOR TREATING GLAUCOMA AND RELATED MINIMALLY INVASIVE GLAUCOMA SURGERY METHOD

RELATED APPLICATIONS

This application claims the benefit of International Patent Application No. PCT/US2019/046999 filed on Aug. 19, 2019 which claims benefit of U.S. Provisional Application No. 62/726,482 filed Sep. 4, 2018, which is incorporated herein by reference.

TECHNICAL FIELD OF INVENTION

The technology of the present disclosure relates generally to an implantable ocular device for treating glaucoma, and a related surgical procedure for implanting the ocular device and using the device for the treatment of glaucoma.

BACKGROUND

It is estimated that approximately three million people in the United States have glaucoma, and more than one hundred thousand people are blind from glaucoma. Glaucoma is the second leading cause of blindness in adult Americans age eighteen to sixty-five and the leading cause of blindness in African Americans.

Glaucoma is an optic neuropathy, or a disorder of the optic nerve, that is characterized by an elevated intraocular pressure. An increase in intraocular pressure may result in changes in the appearance ("cupping") and function ("blind spots") in the visual field of the optic nerve. If the pressure remains high enough for a long enough period of time, total vision loss may occur.

The eye is a hollow structure that contains a clear fluid called aqueous humor. Aqueous humor is continuously produced in the posterior chamber of the eye by the ciliary body. The aqueous humor passes around the lens, through the pupillary opening in the iris and into the anterior chamber of the eye. Once in the anterior chamber, the aqueous humor drains out principally through a canalicular route that involves the trabecular meshwork and Schlemm's canal. The trabecular meshwork and Schlemm's canal are located at a junction between the iris and the cornea called the angle. The trabecular meshwork is composed of collagen beams arranged in a three-dimensional sieve-like structure and lined with a monolayer of trabecular cells. The outer wall of the trabecular meshwork coincides with the inner wall of Schlemm's canal, which is a tube-like structure that runs around the circumference of the cornea.

The aqueous humor, while being filtered, travels through the trabecular meshwork into the Schlemm's canal, then from there through a series of collecting channels and reaches the episcleral venous system to be absorbed. In a healthy individual, aqueous humor production is approximately equal to aqueous humor outflow, and the intraocular pressure therefore remains fairly constant in the 10 to 21 mmHg range. High pressure develops in an eye because of an internal fluid imbalance. In glaucoma, the resistance through the canalicular outflow system is higher than normal causing reduced outflow, thereby causing an internal fluid imbalance and resulting in an increased pressure. In particular, the drainage angle formed by the cornea and the iris remains open, but the microscopic drainage channels in the trabecular meshwork are at least partially obstructed. Other forms of glaucoma may involve decreased outflow through the canalicular pathway due to mechanical blockage, inflammatory debris, cellular blockage and the like.

When the drainage system does not function properly, the aqueous humor cannot filter out of the eye at its normal rate. As the fluid builds up, the intraocular pressure within the eye increases. The increased intraocular pressure compresses the axons of the optic nerve, which carries vision signals from the eye to the brain, and also may compromise the vascular supply to the optic nerve. Damage to the optic nerve is painless and slow, and a vision loss can occur before a person is even aware of a problem.

There are various conventional ways of treating glaucoma. For example, eye and systemic medications are used to treat glaucoma by decreasing the production of aqueous humor or increasing its drainage from the eye.

Surgical treatment may be performed when medications fail to lower the intraocular pressure. For example, surgical procedures may be used to open up the anatomically closed drainage pathways of the aqueous humor to outside the eye. A trabeculectomy is a surgical procedure that creates a pathway for aqueous humor to escape to the surface of the eye. The anterior chamber is entered beneath the scleral flap and a section of deep sclera and trabecular meshwork is excised. Post-operatively, the aqueous humor passes through the resulting hole and collects in an elevated space (subconjunctival reservoir) beneath the conjunctiva. The fluid then is either absorbed through blood vessels in the conjunctiva or traverses across the conjunctiva into the tear film. A deficiency of such procedure is that as the formed bleb is extremely thin, many times it can fail or erupt allowing a pathway for bacteria that normally live on the surface of the eye and eyelids to get into the eye.

Another surgical procedure involves the use of an aqueous shunt. A full thickness hole is made into the eye at the limbus, usually with a needle. The shunt is inserted into the eye through this hole and aqueous humor drains out to the surface of the eye. The tube is attached to a plate and this pate is placed underneath the extraocular muscles. The plate helps to create a reservoir again underneath the conjunctiva to where the aqueous humor drains. Many complications are associated with aqueous shunts. A thickened wall of scar tissue may resist outflow and limit the reduction in eye pressure. The bleb may not form quickly or not at all, resulting in an unrestricted flow through the shunt to the outer surface causing too low of an intraocular pressure that can damage the eye in different ways that could lead to loss of function and sight. As such shunts may erode through the overlying tissues creating an opening to the surface of the eye, a pathway is created for bacteria to get into the eye and endophthalmitis can occur.

Laser surgery is a surgical procedure to reduce the intraocular pressure and includes cyclophotocoagulation (reducing the production of aqueous humor by using a laser to burn the part of the eye that produces aqueous humor), iridotomy (use of a laser to make a hole in the iris to allow fluid to flow more freely in the eye), and trabeculoplasty (use of a laser to create holes in the drainage area of the eye to allow fluid to drain more freely). However, laser surgery is complex and suffers from a variety of deficiencies, including reduced effectiveness, inflammation and related complications.

Accordingly, standard glaucoma surgeries are major surgeries that have significant deficiencies. While such surgeries are very often effective at lowering eye pressure and preventing progression of glaucoma, they have a long list of potential complications. To overcome such deficiencies, more advanced techniques have been developed which are commonly referred to as "minimally invasive glaucoma surgery" or MIGS. MIGS procedures work by using microscopic-sized equipment and tiny incisions. While they reduce the incidence of complications, some degree of effectiveness is also traded for the increased safety.

The MIGS group of operations generally are divided into several categories: miniaturized versions of trabeculectomy; trabecular bypass operations; totally internal or supra-choroidal shunts; milder or gentler versions of laser photocoagulation; and ab-interno canaloplasty (ABiC). Generally, the MIGS procedures work by either bypassing the blocked trabecular meshwork (e.g., trabecular bypass operations and using supra-choroidal shunts), allowing the aqueous humor to drain to another potential space or by opening the Schlemm's canal and the collector channels (ABiC), or by decreasing the production of the aqueous humor (laser photocoagulation). Because of the advantage of MIGS procedures over more conventional treatments, efforts to improve such procedures are on-going.

SUMMARY OF INVENTION

The present invention relates to an ocular device and related minimally invasive glaucoma surgery (MIGS) for treating glaucoma with the ocular device. The described technique includes accessing the Schlemm's canal through a very small guide hole made at the trabecular meshwork. A guide wire, such as for example a suture, probe wire, I-track system or the like, is threaded through the guide hole. A trabecular meshwork bypass device is guided along the guide wire for proper placement for bypassing a blocked portion or portions of the trabecular meshwork. A canaloplasty probing device having a lumen further may be employed to aid insertion of the guide wire and bypass device, and to introduce substances into the trabecular meshwork and/or Schlemm's canal such as glaucoma medications, anti-inflammatory agents, antibiotic releasing pellets, viscoelastic materials and the like.

As the system including the guide wire and bypass device is threaded through the lumen of the probing device (if applicable) or otherwise threaded into the eye through the guide hole, a visualization agent, with or without a viscoelastic substance, is injected into the area in which the bypass device is to be implanted. This allows the Schlemm's canal and the collector channels to be reopened, and also lubricates and expands the Schlemm's canal. The visualization agent may be a dye, such as for example fluoresceine, tripan blue, or other suitable dye, or a physical visible agent such as micro-bubbles. The visualization agent may be visualized using any suitable imaging technique, such as for example optical coherence tomography or ultrasound biomicroscopy. Imaging of the visualization agent flowing through the drainage system allows the Schlemm's canal, trabecular meshwork and the collector channels to be viewed in great detail, which allows the surgeon to further identify the clogged areas of the trabecular meshwork/Schlemm's canal/collector channels versus open channels to ascertain an optimal location for insertion of the bypass device to either bypass the problem or to open the blocked area.

The bypass device includes tips that penetrate through the trabecular meshwork to provide open channels through the trabecular meshwork for draining the aqueous humor. As the Schlemm's canal walls are opened by the viscoelastic and/or the guide wire, this allows easier penetration of the tips of the bypass device through the trabecular meshwork into the Schlemm's canal. Once the bypass device is properly placed, then the guide wire and any canaloplasty probing device are retrieved while leaving the bypass device in place.

In exemplary embodiments, the bypass device has an open tubular structure that is laser cut with pronged features to create open tented holes through the trabecular meshwork. The tubular structure may include multiple arrow-shaped tangs that are formed within a tubular base, with the tubular base having a curvature that approximates a curvature of the iridocorneal angle structures. One or more pairs of adjacent tangs may be flexed at the desired locations to form the tents that are inserted through the trabecular meshwork. In particular, the tents may be formed at clogged locations of the trabecular meshwork as determined by the visualization techniques described above. A heat setting process may be employed to securely implant the tents of the bypass device through the trabecular meshwork. The heat setting process may constitute a lateral angle heat set to impart side-to-side forces during release of the guide wire to create tissue engagement with the trabecular meshwork. In an exemplary embodiment, the arrow-shaped tangs that are used to form the tents may be offset arrows, which may improve holding of the bypass device to the trabecular meshwork.

As an alternative or addition to implantation of a bypass device, the guide wire and canaloplasty probing device may be used to insert glaucoma medication, anti-inflammatory agents, antibiotic releasing pellets, and the like into the trabecular meshwork and/or Schlemm's canal for further success in intra-ocular pressure reduction, and for prevention of inflammation and related complications and infections. In addition, a second guide wire can be threaded through the lumen of the canaloplasty probing device and/or around the canaloplasty probing device to help maintain the efficacy of the Schlemm's canal opening. Studies of prior techniques have demonstrated that de-clogging and maintaining the efficacy of the Schlemm's canal opening aids with long term reduction of intra-ocular pressure.

An aspect of the invention, therefore, is a bypass device that can be implanted into a body tissue to provide fluid channels through the body tissue. In exemplary embodiments, the bypass device includes an open tubular base, and a plurality of pronged features attached to the open tubular base, the pronged features being reconfigurable from a first position to a second position. In the first position the pronged features extend longitudinally along a plane of the open tubular base, and the pronged features are reconfigurable to the second position by flexing the pronged features relative to the tubular base, such that in the second position the pronged features are configured for insertion through the body tissue. The pronged features are associated in pairs, with individual pronged features of a pair of pronged features being attached to each other via a web, and the pronged features are reconfigurable from the first position to the second position by flexing opposing pronged features of the pair about the web to form tent structures. The pronged features may be configured as multiple arrow-shape tangs that are formed within the tubular base, and individual tangs within a pair of tangs may be offset relative to each other along the longitudinal axis of the open tubular base.

Another aspect of the invention is a minimally invasive glaucoma surgery (MIGS) for treating glaucoma using a method of implanting a bypass device into the trabecular meshwork to define a fluid flow channel that permits aqueous humor to pass through trabecular meshwork and into Schlemm's canal. In exemplary embodiments, the MIGS method includes the steps of: providing a bypass device according to any of the embodiments for bypassing a drainage system of an eye including Schlemm's canal, trabecular meshwork, and collector channels; forming a guide hole to access a Schlemm's canal at a trabecular meshwork of an eye; inserting the bypass device through the guide hole and positioning the bypass device within the Schlemm's canal adjacent to the trabecular meshwork; reconfiguring a portion of the pronged features from the first position to the second position to form one or more tent structures; and inserting the one or more tent structures of the bypass device into the trabecular meshwork, wherein the one or more tent structures form tent holes through the trabecular meshwork to define fluid flow channels through the trabecular meshwork. The tenting effect is desired to keep the Schlemm's canal from collapsing or closing, and to maintain the aqueous humor flow through the formed trabecular meshwork openings to the Schlemm's canal and then to the collector channels. The positioning of the bypass device may be aided with the use of a guide wire, and the guide wire and/or bypass device may be inserted through a lumen of a canaloplasty probing device.

Another aspect of the invention is a method of positioning an intraocular device including the steps of: forming a guide hole to access a Schlemm's canal at a trabecular meshwork of an eye; inserting a guide wire through the guide hole; and positioning the intraocular device relative to the guide wire. In exemplary embodiments, the intraocular device is a canaloplasty device having a lumen, and the method further comprises introducing one or more substances into the Schlemm's canal through the lumen. A second guide wire may be threaded through the lumen, or inserted around the canaloplasty device, and the second guide wire aids in maintaining efficacy of the Schlemm's canal opening.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more other embodiments and/or in combination with or instead of the features of the other embodiments.

DETAILED DESCRIPTION OF EMBODIMENTS

Embodiments will now be described with reference to the drawings, wherein like reference numerals are used to refer to like elements throughout. It will be understood that the figures are not necessarily to scale.

Figure 1:
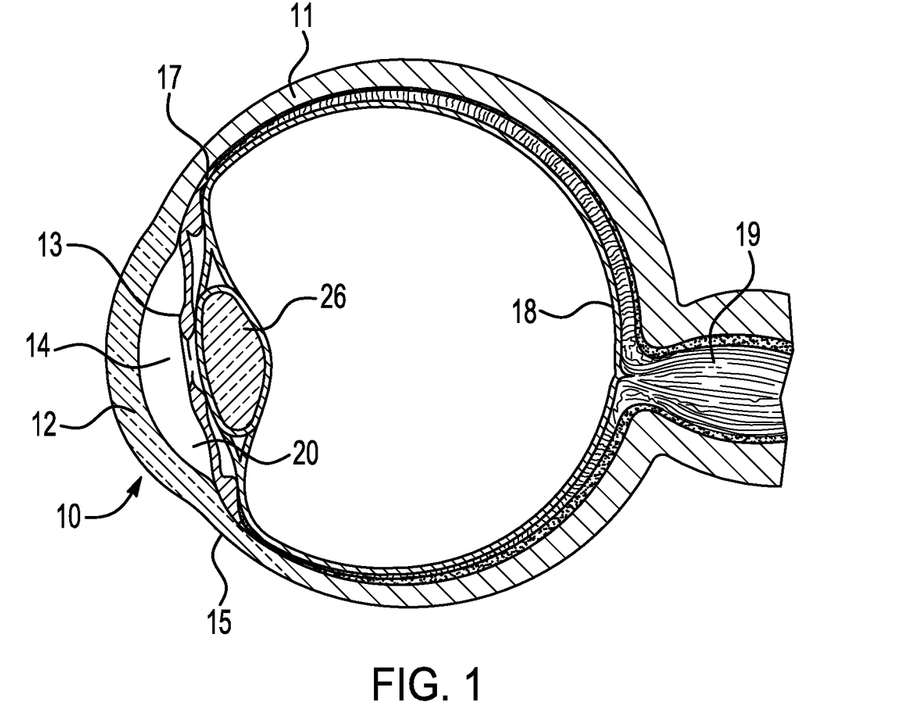
FIG. 1 is a drawing depicting a cross-sectional view of an eye.
Figure 2:
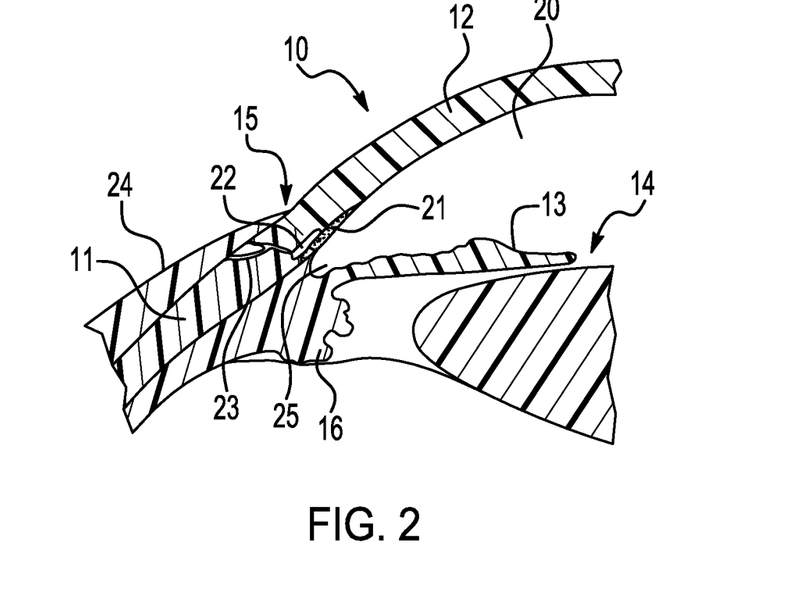
FIG. 2 is a drawing depicting an enlarged cross-sectional view of an anterior chamber angle of the eye of FIG. 1.

FIG. 1 is a drawing depicting a cross-sectional view of an eye 10, and FIG. 2 is a drawing depicting an enlarged cross-sectional view of an anterior chamber angle of the eye of FIG. 1, including the relative anatomical locations of the trabecular meshwork, the anterior chamber, and Schlemm's canal. Collagenous tissue known as sclera 11 covers the eye 10 except the portion covered by the cornea 12. The cornea 12 is a transparent tissue that focuses and transmits light into the eye, and the pupil 14 is the circular hole in the center of the iris 13 (colored portion of the eye). The cornea 12 merges into the sclera 11 at a juncture referred to as the limbus 15. The ciliary body 16 begins internally in the eye and extends along the interior of the sclera 11 and becomes the choroid 17. The choroid 17 is a vascular layer of the eye underlying the retina 18. The optic nerve 19 transmits visual information to the brain and is progressively destroyed by glaucoma as described above.

The anterior chamber 20 of the eye 10, which is bound anteriorly by the cornea 12 and posteriorly by the iris 13 and lens 26, is filled with the aqueous humor. As detailed above, aqueous humor is a fluid produced primarily by the ciliary body 16 and reaches the anterior chamber angle 25 formed between the iris 13 and the cornea 12 through the pupil 14. In a normal eye, the aqueous humor is removed through the trabecular meshwork 21. Aqueous humor passes through the trabecular meshwork 21 into Schlemm's canal 22 and through the aqueous veins 23 which merge with blood-carrying veins and into venous circulation. Intraocular pressure of the eye 10 is maintained by the intricate balance of secretion and outflow of the aqueous humor in the manner described above. Glaucoma is characterized by the excessive buildup of aqueous humor in the anterior chamber 20, which produces an increase in intraocular pressure that ultimately damages and then destroys the optic nerve.

The present invention relates to an intraocular bypass device and related minimally invasive glaucoma surgery (MIGS) for treating glaucoma with an ocular bypass device.

In exemplary embodiments, the bypass device has an open tubular structure that is laser cut with pronged features to create open tented holes through the trabecular meshwork. The tubular structure may include multiple arrow-shaped tangs that are formed within a tubular base, with the tubular base having a curvature that approximates a curvature of the iridocorneal angle structures. One or more pairs of adjacent tangs may be flexed at the desired locations to form the tents that are inserted through the trabecular meshwork. In particular, the tents may be formed at clogged locations of the trabecular meshwork as determined by the visualization techniques described above. A heat setting process may be employed to implant the tents of the bypass device through the trabecular meshwork. The heat setting process may constitute a lateral angle heat set to impart side-to-side forces during release of the guide wire to create tissue engagement. In an exemplary embodiment, the arrow-shaped tangs that are used to form the tents may be offset arrow tangs, which may improve holding upon implantation.

Figure 3:
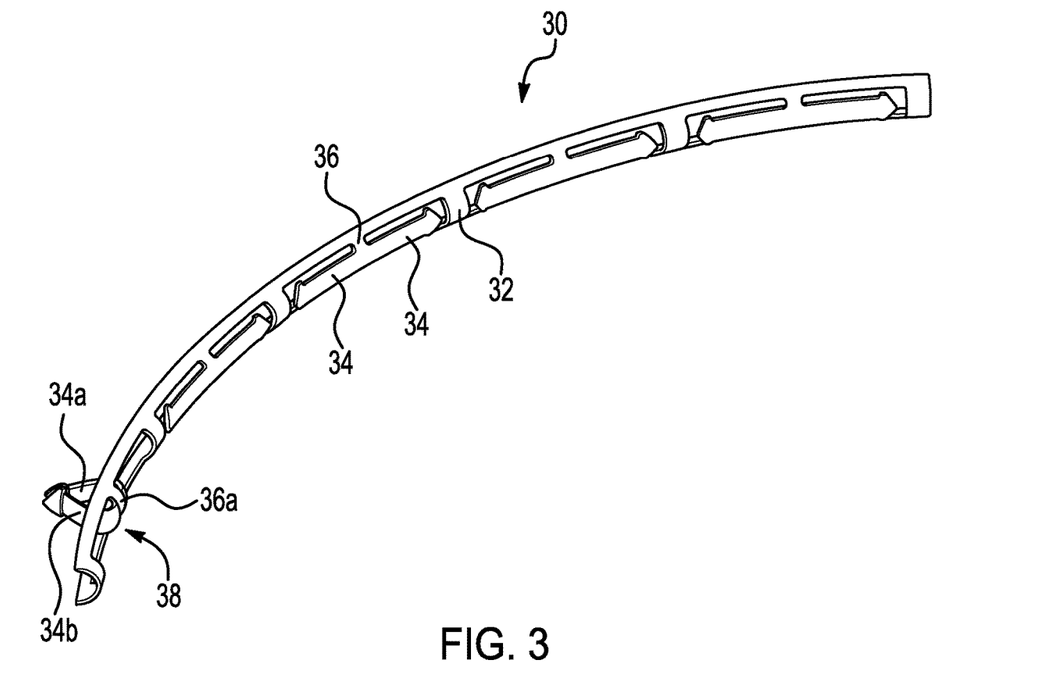
FIG. 3 is a drawing depicting an exemplary bypass device in accordance with embodiments of the present invention.
Figure 4:
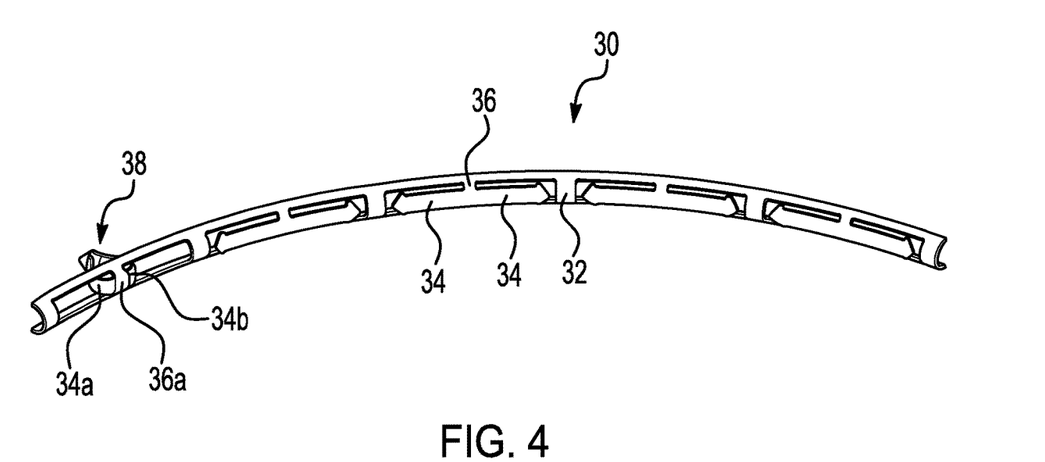
FIG. 4 is a drawing depicting another view of the exemplary bypass device of FIG. 3.

FIG. 3 is a drawing depicting an exemplary bypass device 30 in accordance with embodiments of the present invention, and FIG. 4 is a drawing depicting another view of the exemplary bypass device of FIG. 3. The bypass device 30 includes an open tubular base 32 that is formed with a curvature approximating the curvature of typical iridocorneal angle structures. The bypass device further is formed to include a plurality of pronged features 34 that are attached to the open tubular base and are reconfigurable from a first position to a second position. In the first position, the pronged features 34 generally extend longitudinally along a plane of the tubular base 32. The pronged features then are reconfigurable from the first position to the second position by flexing the pronged features relative to the tubular base 32, such that in the second position the pronged features are configured for insertion through a body tissue. For example, the pronged features in the second position may constitute tent structures that operate to create open tented holes through the trabecular meshwork as further detailed below. The bypass device may be formed using any suitable manufacturing process. Examples without limitation include laser cutting, photo-chemical etching, electrical discharge machining (EDM) or micro-machining, and micro-molding out of a plastic substrate.

In exemplary embodiments, the pronged features 34 are associated in pairs connected to the tubular base 32 via a web 36. Individual pronged features of a pair of pronged features thus are attached to each other via the web 36. Further as to each associated pair, the pronged features are reconfigurable from the first position to the second position by flexing opposing pairs of pronged features 32 toward each other about the web 36. Materials that are used to form the bypass implant include, for example, nitinol, platinum, titanium, stainless steel, gold, silicon, PMMA, polyimide, or like materials. In an exemplary embodiment, the bypass implant material is nitinol and the shape is heat set in three stages to form the tangs and curvature. A common base fixture may be used for all three heat setting stages, but in a different configuration or orientation, and the heat setting may be achieved at 525° C. for seven minutes per stage.

In the example shown in FIGS. 3 and 4, an exemplary pair of pronged features 34a and 34b are flexed around their associated web 36a to form a tent structure 38, which in turn is used to form the referenced tented holes through the trabecular meshwork (again as further detailed below). Although only one tent structure 38 is shown in these figures, any suitable number of tents 38 may be formed as desired for any particular circumstance, and thus a portion of the pronged features may be reconfigured to the second position while a portion of the pronged features are maintained in the first position. In general, tent structures may be formed to be positioned at clogged locations of the trabecular meshwork as determined by the visualization techniques. In this manner, fluid can pass through the clogged portion(s) of the trabecular meshwork through the tented holes formed by the tent structures 38.

Figure 5:
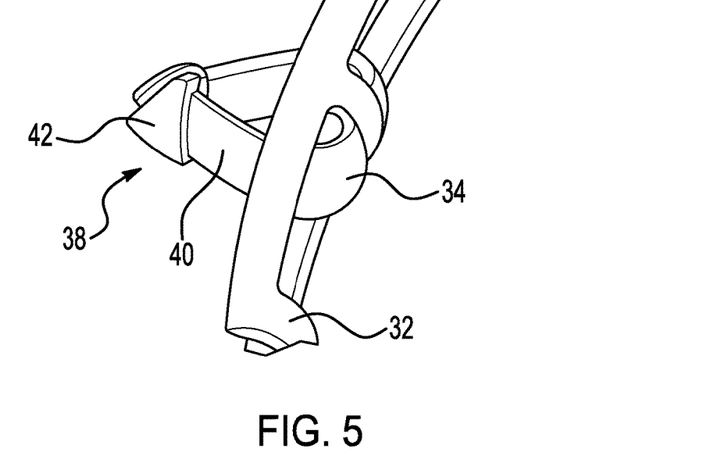
FIG. 5 is a drawing depicting a close-up view of a tent structure of the bypass device depicted in FIGS. 3 and 4.

FIG. 5 is a drawing depicting a close-up view of the tent structure 38 of the bypass device depicted in FIGS. 3 and 4. In exemplary embodiments, the pronged features 34 are configured as multiple arrow-shaped tangs that are formed within the tubular base 32. Each of the tangs 34 includes a neck 40 that is flexible relative to the tubular base 32, and an arrow-shaped head 42 that is flexible relative to the neck 40. The flexing of the arrow-shaped heads 42 relative to the neck 40 permits optimal positioning of the tent structure 38 for proper insertion through the trabecular meshwork to form the tented holes therethrough. In addition, the arrow shape of the heads 42 provides a wedge configuration for penetration of the tent structure 38 through the trabecular meshwork to form said tented holes. Once implanted within the trabecular meshwork, the tent structures 38 each defines a fluid flow channel that permits aqueous humor to pass through clogged portion(s) of the trabecular meshwork and into Schlemm's canal.

With such a configuration, one or more openings are provided in fluid communication with one or more intrinsic internal chambers of the device. The internal chamber(s) are also in fluid communication with one or more openings which are likewise in fluid communication with Schlemm's canal or other ocular areas so as to allow passage of fluid from the anterior chamber of the eye.

Figure 6:
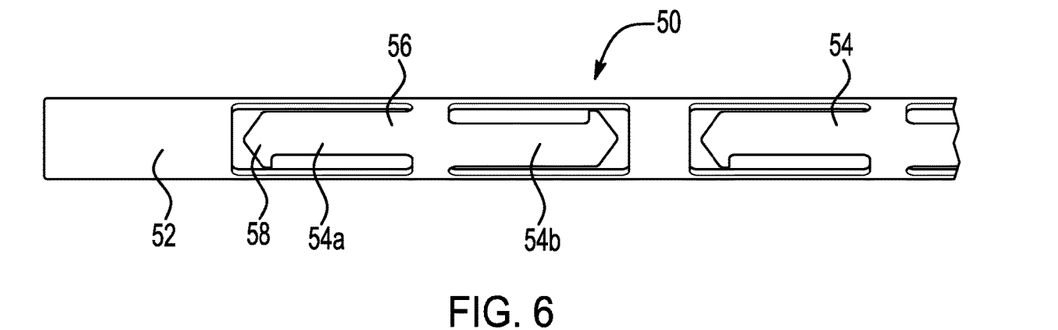
FIG. 6 is a drawing depicting another configuration of an exemplary bypass device in accordance with embodiments of the present invention.

FIG. 6 is a drawing depicting another configuration of an exemplary bypass device 50 in accordance with embodiments of the present invention. Similarly, as in the previous embodiment, the bypass device 50 includes an open tubular base 52 that is laser cut with a curvature approximating the curvature of typical iridocorneal angle structures. The bypass device 50 further is laser cut to include pronged features 54 that are reconfigurable from a first position to a second position by flexing the pronged features to form tent structures in a comparable manner as described above. The pronged features 54 also may be configured as multiple arrow-shaped tangs that are formed within the tubular base 52. Each of the tangs 54 includes a neck 56 that is flexible relative to the tubular base 52, and an arrow-shaped head 58 that is flexible relative to the neck 56 for optimal positioning of tent structures formed with the tangs 54 with respect to clogged portions of the trabecular meshwork. As compared to the previous embodiment, in the embodiment of FIG. 6 the arrow-shaped tangs 54 that are used to form the tent structures are offset arrow tangs, i.e., opposing tangs 54a and 54b are offset relative to each other along the longitudinal axis of the tubular base 52. Accordingly, individual tangs within a pair of opposing tangs are offset relative to each along the longitudinal axis of the open tubular base. The offset tang configuration of FIG. 6 may improve holding of the bypass device 52 within the trabecular meshwork upon implantation. Also, the tangs can be made in different sizes and shapes, and/or oriented in different directions, to provide a better positioning and secure hold of the device to stay in place after insertion.

Figure 7:
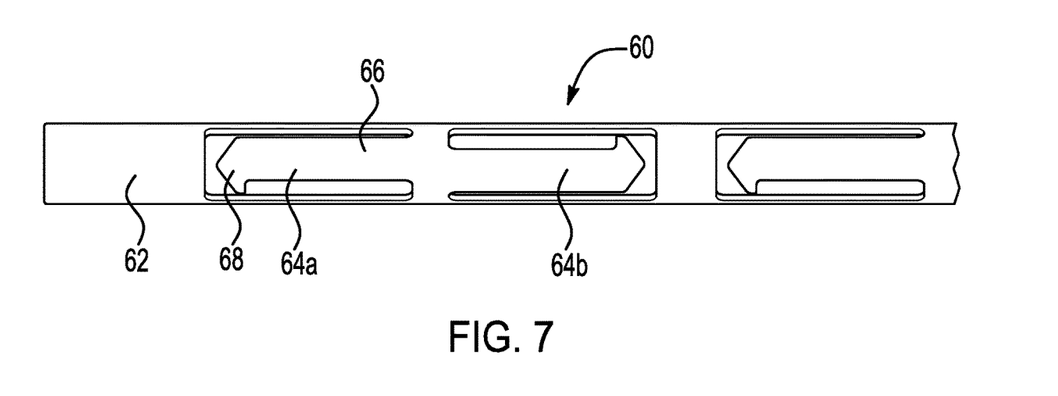
FIG. 7 is a drawing depicting another configuration of an exemplary bypass device in accordance with embodiments of the present invention.

FIG. 7 is a drawing depicting another configuration of an exemplary bypass device 60 in accordance with embodiments of the present invention. Similarly as in the previous embodiments, the bypass device 60 includes an open tubular base 62 that is laser cut with a curvature approximating the curvature of typical iridocorneal angle structures. The bypass device 60 further is laser cut to include pronged features 64 that are reconfigurable from a first position to a second position by flexing the pronged features to form tent structures in a comparable manner as described above. The pronged features 64 also may be configured as multiple arrow-shaped tangs that are formed within the tubular base 62. Each of the tangs 64 includes a neck 66 that is flexible relative to the tubular base 62, and an arrow-shaped head 68 that is flexible relative to the neck 66 for optimal positioning of tent structures formed with the tangs 64 with respect to clogged portions of the trabecular meshwork. Similarly as in the previous embodiment, in the embodiment of FIG. 7 the arrow-shaped tangs 64 that are used to form the tent structures also are offset arrow tangs, i.e., opposing tangs 64a and 64b are offset relative to each other along the longitudinal axis of the tubular base 62. The embodiment 60 of FIG. 7 differs from the embodiment 50 of FIG. 6 in that the tangs 64 are longer in the longitudinal direction as compared to the tangs 54 of FIG. 6. Accordingly, tent structures formed from the tangs 64 of FIG. 7 will extend father from the tubular base as compared to the tangs 54 of FIG. 6.

Figure 8:
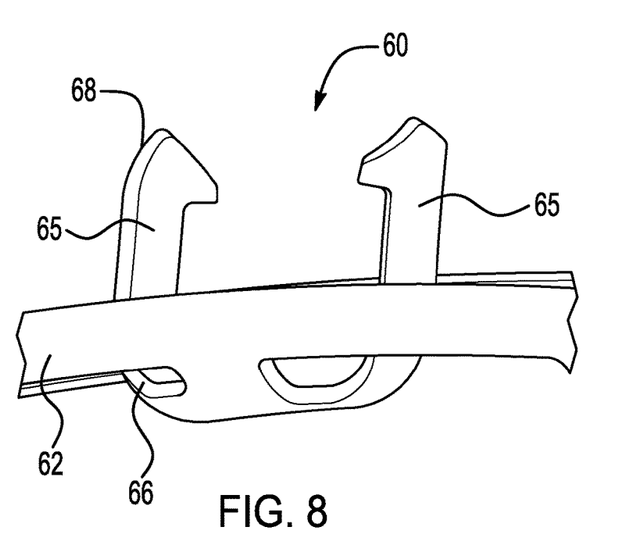
FIG. 8 is a drawing depicting a close-up view of bent tangs of the bypass device depicted in FIG. 7, which may be employed to form a tent structure.

FIG. 8 is a drawing depicting a close-up view of bent tangs 65 of the bypass device 60 depicted in FIG. 7, which may be employed to form a tent structure. Similarly as described above in connection with previous embodiments, the flexing of the arrow-shaped heads 68 relative to the neck 66 permits optimal positioning of the tent structure 65 for proper insertion through the trabecular meshwork to form the tented holes therethrough. In addition, the arrow shape of the heads 68 provide a wedge configuration for penetration of the tent structure through the trabecular meshwork to form the referenced tented holes. Once implanted within the trabecular meshwork, the tent structures each defines a fluid flow channel that permits aqueous humor to pass through clogged portion(s) of the trabecular meshwork and into Schlemm's canal.

Figure 9:
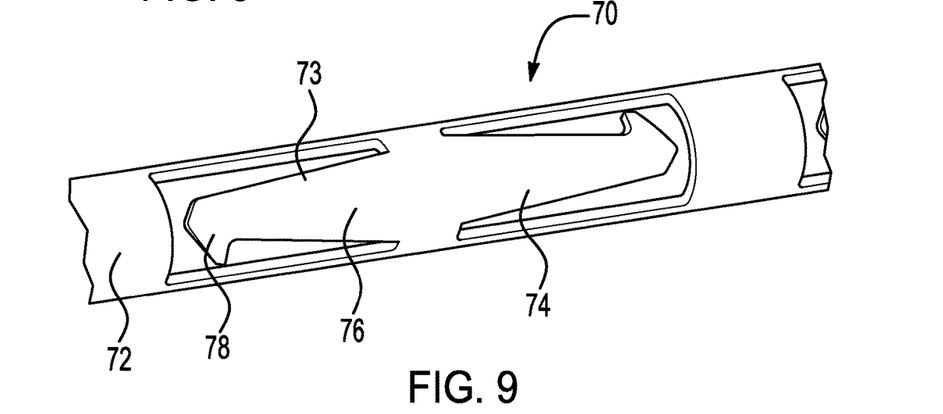
FIG. 9 is a drawing depicting another configuration of an exemplary bypass device in accordance with embodiments of the present invention.
Figure 10:
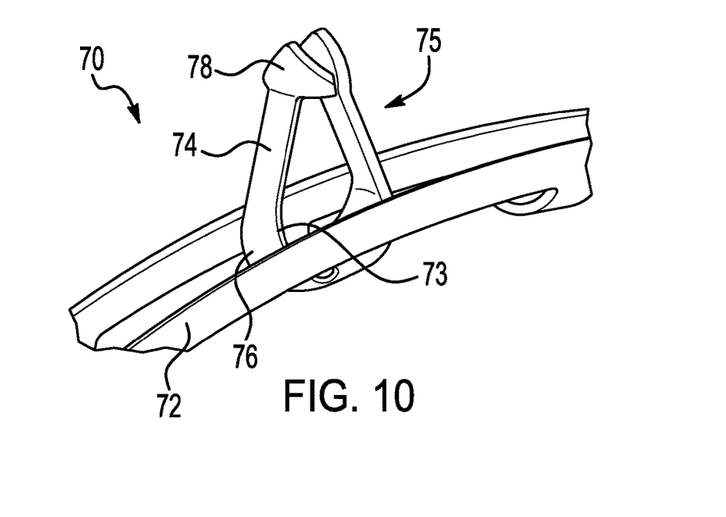
FIG. 10 is a drawing depicting a close-up view of a tent structure of the bypass device depicted in FIG. 9.

FIG. 9 is a drawing depicting another configuration of an exemplary bypass device 70 in accordance with embodiments of the present invention. FIG. 10 is a drawing depicting a close-up view of a tent structure 75 of the bypass device depicted in FIG. 9. Similarly as in the previous embodiments, the bypass device 70 includes an open tubular base 72 that is laser cut with a curvature approximating the curvature of typical iridocorneal angle structures. The bypass device 70 further is laser cut to include pronged features 74 that are reconfigurable from a first position to a second position by flexing the pronged features to form tent structures in a comparable manner as described above. The pronged features 74 also may be configured as multiple arrow-shaped tangs that are formed within the tubular base 72. Each of the tangs 74 includes a neck 76 that is flexible relative to the tubular base 72, and an arrow-shaped head 78 that is flexible relative to the neck 76 for optimal positioning of tent structures 75 formed with the tangs 74 with respect to clogged portions of the trabecular meshwork. The embodiment 70 of FIGS. 9 and 10 differs from previous embodiments in that the tangs 74 may include a tapered edge 73 that runs from the tubular base 72 to the arrow-shaped head 78. The tapered edges may aid in manipulation and bending to form the tent structures 75.

Figures 11, 12, 13:
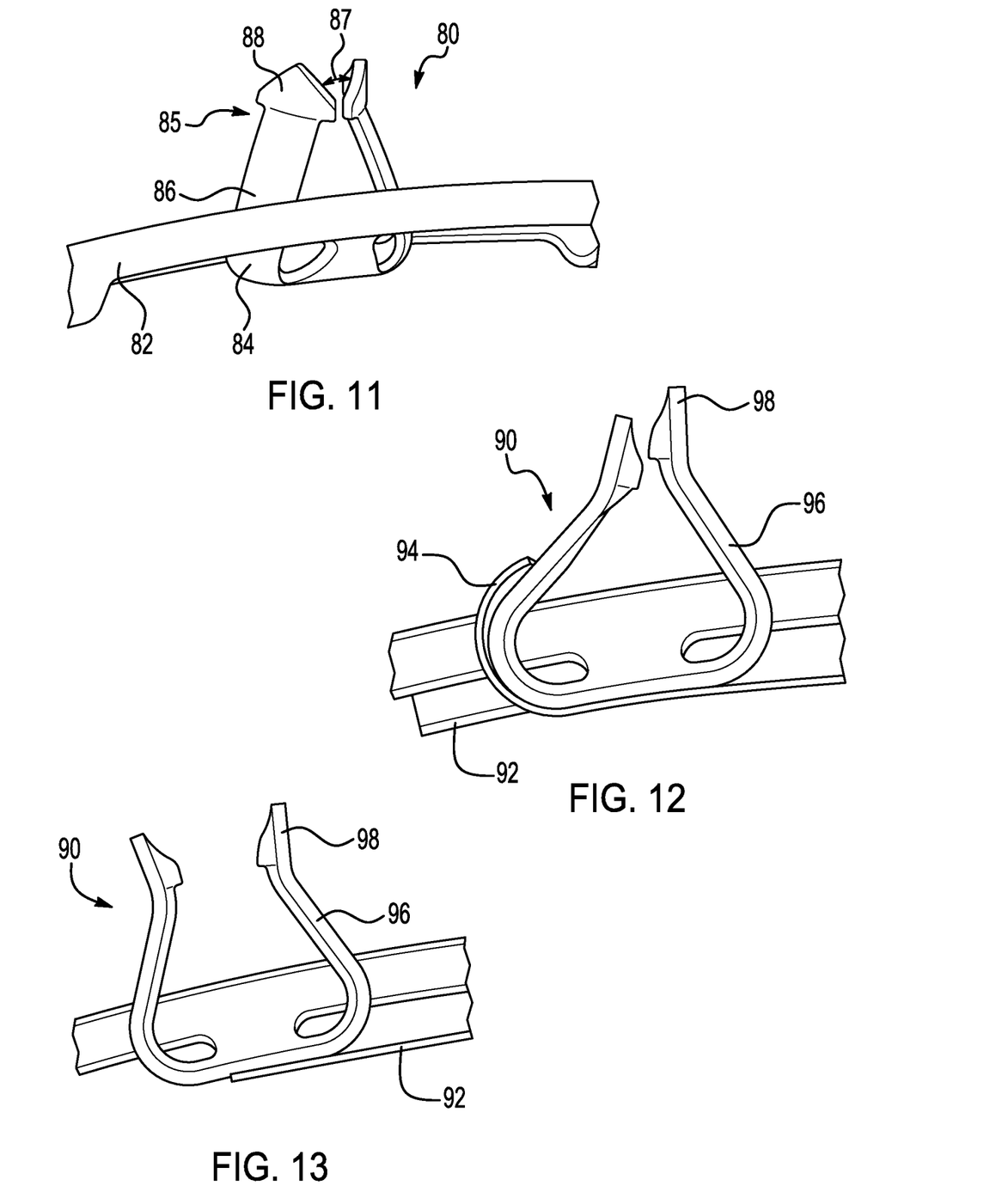
FIG. 11 is a drawing depicting a close-up view of a variation of a tent structure of a bypass device in accordance with embodiments of the present invention.
FIG. 12 and FIG. 13 are drawings depicting a first method of inserting a bypass device in accordance with embodiments of the present invention.

FIG. 11 is a drawing depicting a close-up view of a variation of a tent structure 85 of a bypass device 80 in accordance with embodiments of the present invention. Similarly as in the previous embodiments, the bypass device 80 includes an open tubular base 82 that is laser cut with a curvature approximating the curvature of typical iridocorneal angle structures. The bypass device 80 further is laser cut to include pronged features 84 that are reconfigurable from a first position to a second position by flexing the pronged features to form tent structures in a comparable manner as described above. The pronged features 84 also may be configured as multiple arrow-shaped tangs that are formed within the tubular base 82. Each of the tangs 84 includes a neck 86 that is flexible relative to the tubular base 82, and an arrow-shaped head 88 that is flexible relative to the neck 86 for optimal positioning of tent structures 85 formed with the tangs 84 with respect to clogged portions of the trabecular meshwork. The embodiment 80 of FIG. 11 differs from previous embodiments in that opposing tangs 84 are oriented at an angle 87 relative to each other upon formation of the tent structure 85. The angled structure may be incorporated into any of the previous embodiments, and may provide enhanced retention of the bypass device within the ocular tissue.

FIGS. 12 and 13 are drawings depicting a first method of inserting a bypass device in accordance with embodiments of the present invention. In this example, a bypass device 90 is guided during insertion within a sheath 92. The bypass device 90 may be configured in accordance with any of the embodiments. As shown in FIG. 12, the sheath 92 may include a shoulder 94 that acts to curl and otherwise shape tangs 96 of the bypass device to form the tent structures. FIG. 12 illustrates a tent position under operation of the shoulder 94 of the sheath 92, and the bypass device may be inserted through the trabecular meshwork while in this tent position. The tangs 96 of the bypass device may have properties of a spring, and thus the curling force acts against a spring action that biases the tangs outward from the tent structure shown in FIG. 12. Accordingly, as shown in FIG. 13, once the curling force applied by the shoulder of the sheath is removed, the spring action of the tangs 96 results in the tangs restoring to a set position in which the arrow heads 98 of the tangs are spaced farther apart as compared to the tent position of FIG. 12. In operation of the bypass device 90 once implanted, the restoration to the set position widens the bypass hole through the trabecular meshwork, which aids in the draining of fluid.

Figure 14:
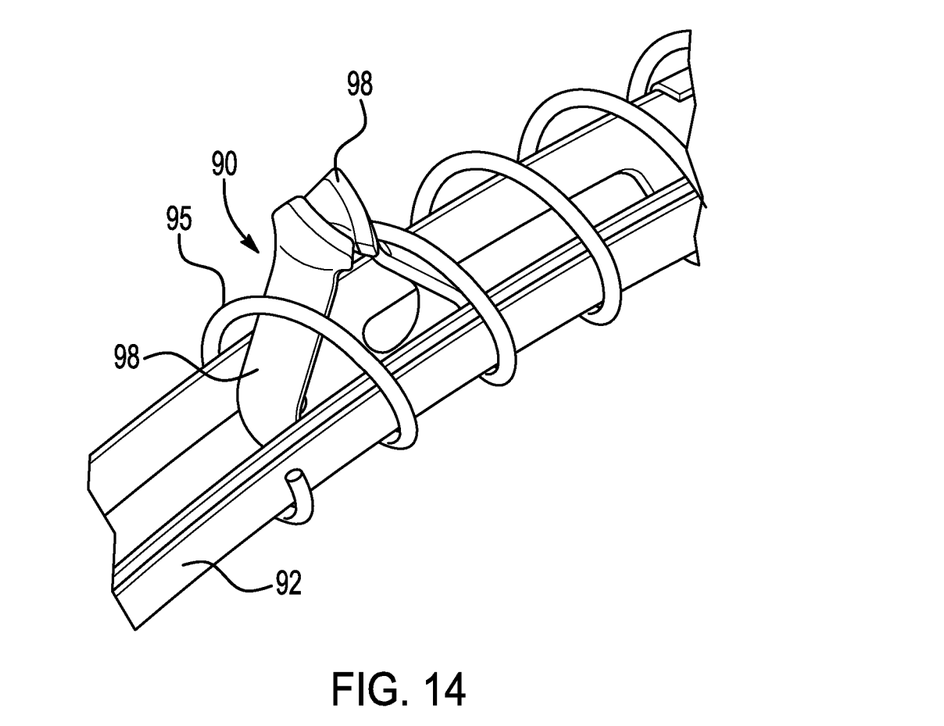
FIG. 14 is a drawing depicting a second method of inserting a bypass device in accordance with embodiments of the present invention.

FIG. 14 is a drawing depicting a second method of inserting a bypass device in accordance with embodiments of the present invention. In this embodiment, the sheath 92 is equipped with a coil spring 95 rather than the shoulder 94 of the previous embodiment. As the bypass device 90 is moved into position, the turns of the coil spring 95 interact against the tangs 96 to form the tent configuration as shown in the figure. When the sheath portion with coil spring 95 is removed from interaction with the tangs 96, similarly as in the previous embodiment, the curling force applied by the coil spring of the sheath is removed, and the spring action of the tangs 96 results in the tangs restoring to the set position illustrated in FIG. 13. Again, the restoration to the set position widens the bypass hole through the trabecular meshwork, which aids in the draining of fluid.

Another aspect of the invention is a minimally invasive glaucoma surgery (MIGS) for treating glaucoma using a method of implanting a bypass device into the trabecular meshwork to define a fluid flow channel that permits aqueous humor to pass through trabecular meshwork and into Schlemm's canal. As referenced above, one or more pairs of adjacent pronged features may be reconfigured at the desired locations, and in particular at clogged locations of the trabecular meshwork, to form the tent structures that are inserted into the trabecular meshwork to form the tent holes through the trabecular meshwork. In particular, the tent structures may be formed at clogged locations of the trabecular meshwork as determined by visualization techniques. The spring action of the tangs may be used as a widening step to widen the holes through the trabecular meshwork to enhance the fluid flow. A heat setting process may be employed to securely implant the tent structures of the bypass device through the trabecular meshwork, such that the tent structures form the referenced tent holes for fluid flow through the trabecular meshwork. The implantation of the bypass device may be aided by using a guide wire sheath to position the bypass device at the desired location within the trabecular meshwork. The heat setting process may constitute a lateral angle heat set to impart side-to-side forces during release of the guide wire to create tissue engagement.

In exemplary embodiments, therefore, the MIGS method includes the steps of: providing a bypass device for bypassing a drainage system of an eye including Schlemm's canal, trabecular meshwork, and collector channels according to any of the embodiments; forming a guide hole to access a Schlemm's canal at a trabecular meshwork of an eye; inserting the bypass device through the guide hole and positioning the bypass device within the Schlemm's canal adjacent to the trabecular meshwork; reconfiguring a portion of the pronged features from the first position to the second position to form one or more tent structures; and inserting the one or more tent structures of the bypass device into the trabecular meshwork, wherein the one or more tent structures form tent holes through the trabecular meshwork to define fluid flow channels through the trabecular meshwork. The positioning of the bypass device may be aided with the use of a guide wire.

In an exemplary embodiment, an incision may be made to form a guide hole to provide access to a portion of the Schlemm's canal. The bypass device, and optionally a guide wire sheath, are inserted through the guide hole such that the curvature of the bypass device is generally aligned with the curvature of the Schlemm's canal. The guide wire may be used to aid in proper positioning of the bypass device, such that tent structures are optimally positioned relative to clogged portions of the trabecular meshwork as determined by any suitable visual technique. The guide wire particularly may be suitable for use when a larger number of tent structures, such as three or more for example, are employed. Once the bypass device is properly positioned, a heat setting process may be employed to secure the bypass device within the tissue of the trabecular meshwork. As referenced above, the heat setting process may constitute a lateral angle heat set to impart side-to-side forces during release of the guide wire to create tissue engagement of the bypass device with the trabecular meshwork. With such placement, the tent structures each defines a fluid flow channel that permits aqueous humor to pass through trabecular meshwork and into Schlemm's canal.

More specifically, a MIGS glaucoma procedure includes accessing the Schlemm's canal through a very small guide hole made at the trabecular meshwork. A guide wire, such as for example a suture, probe wire, I-track system or the like, is threaded through the guide hole. The trabecular meshwork bypass device according to any of the embodiments is guided along the guide wire for proper placement for bypassing a blocked portion or portions of the trabecular meshwork. A canaloplasty probing device having a lumen further may be employed to aid insertion of the guide wire and bypass device, and to introduce substances into the trabecular meshwork and/or Schlemm's canal such as glaucoma medication, anti-inflammatory agents, antibiotic releasing pellets, and the like.

As the system including the guide wire and bypass device is threaded through the lumen of the canaloplasty probing device (if applicable), or otherwise threaded into the eye through the guide hole, a visualization agent with or without a viscoelastic substance is injected in the area in which the bypass device is to be implanted. This allows the Schlemm's canal and the collector channels to be reopened, and also lubricates and expands the Schlemm's canal to facilitate implantation of the bypass device. The visualization agent may be a dye, such as for example fluoresceine, tripan blue, or other suitable dye, or a physical visible agent such as micro-bubbles. The visualization agent may be visualized using any suitable imaging technique, such as for example optical coherence tomography or ultrasound bio-microscopy or direct visualization via magnification. Imaging of the visualization agent flowing through the collector channels allows the surgeon to further identify the clogged areas of the trabecular meshwork/Schlemm's canal/collector channels versus open structures to ascertain an optimal location for insertion of the bypass device.

The bypass device is inserted through the trabecular meshwork, whereby the tent holes are formed through the trabecular meshwork to provide open channels for draining the aqueous humor. As the Schlemm's canal walls are opened by the viscoelastic and/or the guide wire, this allows easier penetration of the tips of the bypass device through the trabecular meshwork into the Schlemm's canal. Once the bypass device is properly placed, then the guide wire and any canaloplasty probing device are retrieved while leaving the bypass device in place. In one exemplary embodiment, the guide wire is inserted into a superior portion of the Schlemm's canal, and the bypass device thus is positioned inferior to the guide wire. Alternatively, the guide wire may be inserted into an inferior portion of the Schlemm's canal, and the bypass device thus is positioned superior to the guide wire.

Figure 15:
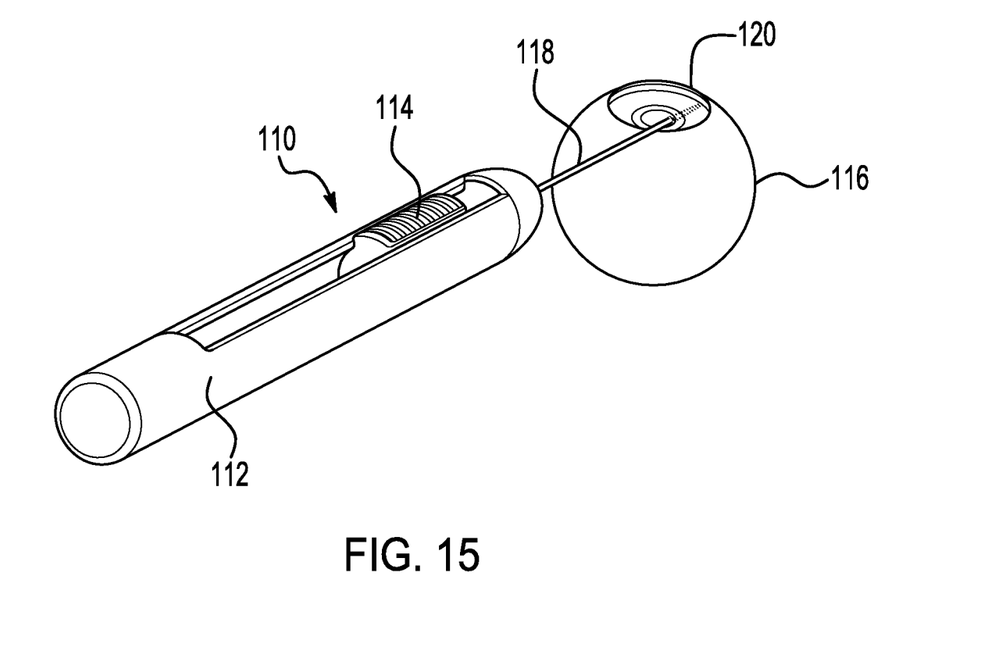
FIG. 15 is a drawing depicting an exemplary insertion instrument for inserting a bypass device in accordance with embodiments of the present invention.
Figure 16:
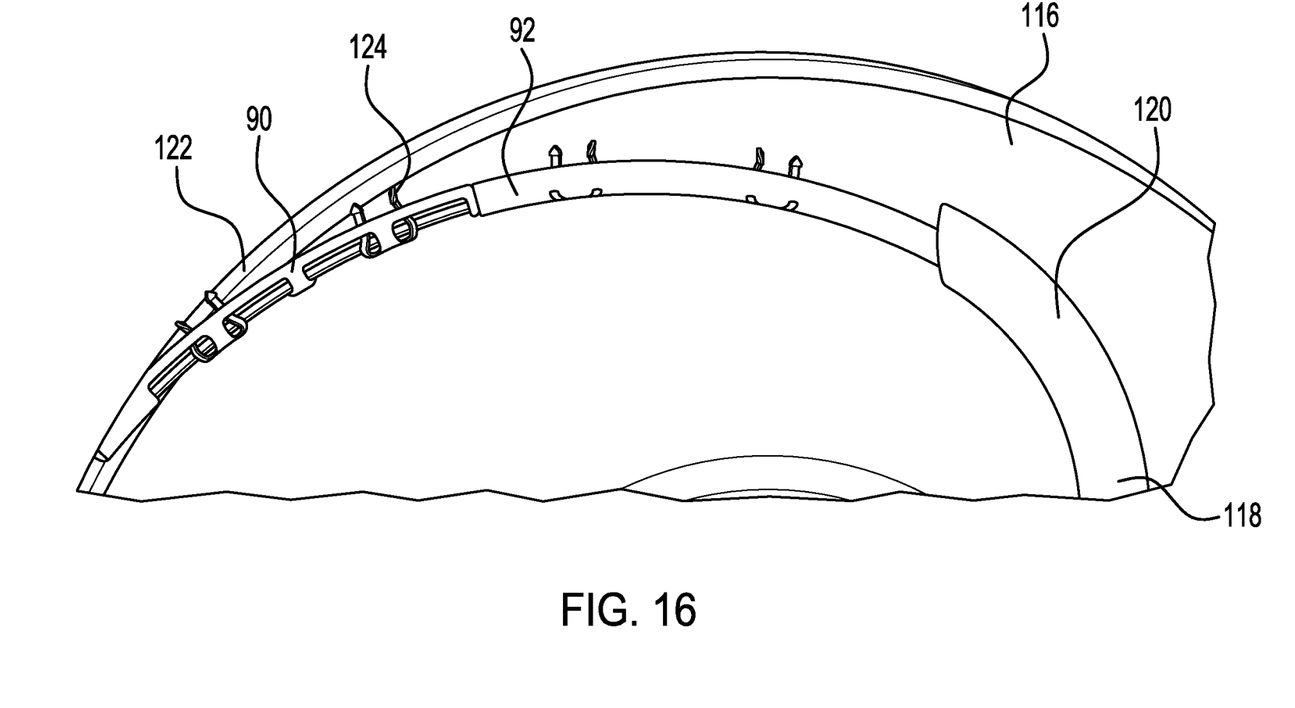
FIG. 16 is a drawing depicting an insertion operation of a bypass device which may be performed using the insertion instrument of FIG. 15.

FIG. 15 is a drawing depicting an exemplary insertion instrument 110 for inserting a bypass device in accordance with embodiments of the present invention. FIG. 16 is a drawing depicting the insertion operation of a bypass device 90 (which may be configured according to any of the embodiments) which may be performed using the insertion instrument 110 of FIG. 15. It will be appreciated that the insertion instrument 110 is a suitable example, and other suitable instruments may be employed. As illustrated in FIG. 15, the exemplary insertion instrument 110 includes a handle portion 112 with a slider 114 that may be used to drive the bypass device into position within an eye 116. For insertion, a bypass device 90 according to any of the embodiments is housed within a sheath 92 that is comparable to the sheath 92 shown in FIGS. 12-14, with the sheath 92 acting as a guide wire. The combined sheath and bypass device are threaded through a curved cannula 118 that houses the bypass device until deployment at the desired position within the eye. A groove in the cannula 118 orients the tangs of the bypass device for implanting. Using the slider 114, a surgeon advances the bypass device through the cannula 118 to a curved end portion 120 of the cannula.

As best shown in FIG. 16, the curved end portion 120 of the cannula 118 provides support to push the bypass device 90 into the trabecular meshwork 122. In particular, the curved shape allows the cannula to provide a force vector in line with any of the tangs during insertion into the trabecular meshwork. FIG. 16 illustrates tangs of the bypass device 90 formed into tent structures 124, with the tent structures 124 being formed for example by one of the methods described above with respect to FIGS. 12-14. Once the bypass device 90 is properly positioned and inserted through the trabecular meshwork 122, the slider 114 is employed to withdraw the sheath 92 through the cannula 118, leaving the bypass device 90 in place. With the sheath removed, the spring action of the tangs results in restoration of the tent structures to the widened set position configuration of FIG. 13, thereby providing effective retention and adequate holes through the trabecular meshwork for fluid draining.

An alternative or addition to implantation specifically of a bypass device, comparable principles may be employed by which a guide wire is used to guide positioning of any suitable intraocular device. For example, the guide wire may be employed to guide a canaloplasty probing device to insert glaucoma medication, anti-inflammatory agents, antibiotic releasing pellets, and the like into the trabecular meshwork and/or Schlemm's canal for further success in intra-ocular pressure reduction, and for prevention of inflammation and related complications and infections. In addition, a second guide wire can be threaded through the lumen of the canaloplasty probing device or around the canaloplasty probing device to help maintain the efficacy of the Schlemm's canal opening. Studies of prior techniques have demonstrated that de-clogging and maintaining the efficacy of the Schlemm's canal opening aids with long term reduction of intra-ocular pressure.

In addition, although the bypass device has been described specifically in connection with forming fluid channels through the trabecular meshwork as part of a MIGS glaucoma treatment, comparable principles may be applicable to forming fluid channels through any suitable body tissue. Accordingly, use of the bypass device and the related methods of implanting the bypass device are not limited to the trabecular meshwork and components of the eye, but may be employed in other circumstances in which it desired to form fluid channels through a body tissue.

An aspect of the invention, therefore, is a bypass device that can be implanted into a body tissue to provide fluid channels through the body tissue. In exemplary embodiments, the bypass device includes an open tubular base, and a plurality of pronged features attached to the open tubular base, the pronged features being reconfigurable from a first position to a second position. In the first position the pronged features extend longitudinally along a plane of the open tubular base, and the pronged features are reconfigurable to the second position by flexing the pronged features relative to the tubular base, such that in the second position the pronged features are configured for insertion through the body tissue. The bypass device may include one or more of the following features, either individually or in combination.

In an exemplary embodiment of the bypass device, the pronged features are associated in pairs, with individual pronged features of a pair of pronged features being attached to each other via a web, and the pronged features are reconfigurable from the first position to the second position by flexing opposing pronged features of the pair about the web.

In an exemplary embodiment of the bypass device, the pronged features are configured as multiple arrow-shape tangs that are formed within the tubular base.

In an exemplary embodiment of the bypass device, each arrow-shaped tang includes a neck that is flexible relative to the tubular base, and an arrow-shape head that is flexible relative to the neck.

In an exemplary embodiment of the bypass device, individual tangs within a pair of opposing tangs are offset relative to each other along the longitudinal axis of the open tubular base.

In an exemplary embodiment of the bypass device, each individual tang includes a tapered edge that runs from the tubular base to an arrow-shaped head of the tang.

In an exemplary embodiment of the bypass device, opposing ends of the pronged features are oriented at an angle relative to each other upon formation of the tent structures.

In an exemplary embodiment of the bypass device, the pronged features have a spring action such that when a force creating a respective tent structure is released, the pronged structures restore to a set position in which heads of the pronged structures are spaced farther apart as compared to the tent structure.

In an exemplary embodiment of the bypass device, in the second position the pronged features are configured as tent structures.

In an exemplary embodiment of the bypass device, the tubular base has a curvature that approximates a curvature of iridocorneal angle structures.

In an exemplary embodiment of the bypass device, portions of the pronged features are reconfigured to the second position and portions of the pronged features are maintained in the first position.

Another aspect of the invention is a minimally invasive glaucoma surgery (MIGS) for treating glaucoma using a method of implanting a bypass device into the trabecular meshwork to define a fluid flow channel that permits aqueous humor to pass through trabecular meshwork and into Schlemm's canal. In exemplary embodiments, the MIGS method includes the steps of: providing a bypass device according to any of the embodiments for bypassing a drainage system of an eye including Schlemm's canal, trabecular meshwork, and collector channels; forming a guide hole to access a Schlemm's canal at a trabecular meshwork of an eye; inserting the bypass device through the guide hole and positioning the bypass device within the Schlemm's canal adjacent to the trabecular meshwork; reconfiguring a portion of the pronged features from the first position to the second position to form one or more tent structures; and inserting the one or more tent structures of the bypass device into the trabecular meshwork, wherein the one or more tent structures form tent holes through the trabecular meshwork to define fluid flow channels through the trabecular meshwork. The MIGS method may include one or more of the following features, either individually or in combination.

In an exemplary embodiment of the MIGS method, the method further includes performing a visualization technique to locate clogged portions of the drainage system, wherein the bypass device is aligned relative to the trabecular meshwork such that the one or more tent structures are positioned at or adjacent to respective clogged portions of the trabecular meshwork as determined by the visualization technique.

In an exemplary embodiment of the MIGS method, the method further includes performing a heat setting process to securely implant the tent structures in the trabecular meshwork.

In an exemplary embodiment of the MIGS method, the method further includes inserting a guide wire through the guide hole, positioning the bypass device relative to the guide wire, and removing the guide wire once the bypass device is properly positioned.

In an exemplary embodiment of the MIGS method, the guide wire is inserted into a superior portion of the Schlemm's canal, and the bypass device is positioned inferior relative to the guide wire.

In an exemplary embodiment of the MIGS method, the guide wire is inserted into an inferior portion of the Schlemm's canal, and the bypass device is positioned superior relative to the guide wire.

In an exemplary embodiment of the MIGS method, the method further includes performing a heat setting process to securely implant the tent structures in the trabecular meshwork, wherein the heat setting process includes a lateral angle heat set to impart side-to-side forces during release of the guide wire to create tissue engagement of the bypass device with the trabecular meshwork.

In an exemplary embodiment of the MIGS method, the method further includes injecting a viscoelastic substance into the Schlemm's canal to expand the Schlemm's canal to aid inserting the bypass device.

In an exemplary embodiment of the MIGS method, the method further includes inserting a canaloplasty device having a lumen through the guide hole, introducing one or more substances into the Schlemm's canal through the lumen, and removing the canaloplasty device after inserting the bypass device into the trabecular meshwork.

In an exemplary embodiment of the MIGS method, the one or more substances include a guide wire to aid in positioning the bypass device, glaucoma medication, anti-inflammatory agents, and/or antibiotic releasing pellets.

Another aspect of the invention is a method of positioning an intraocular device including the steps of: forming a guide hole to access a Schlemm's canal at a trabecular meshwork of an eye; inserting a guide wire through the guide hole; and positioning the intraocular device relative to the guide wire. In exemplary embodiments, the intraocular device is a canaloplasty device having a lumen, and the method further comprises introducing one or more substances into the Schlemm's canal through the lumen. A second guide wire may be threaded through the lumen, or inserted around the canaloplasty device, and the second guide wire aids in maintaining efficacy of the Schlemm's canal opening.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or to embodiments of the invention. In addition, while a particular feature of the invention may have been described above with respect to only one or more of several embodiments, such feature may be combined with one or more other features of the other embodiments, as may be desired and advantageous for any given or particular application.

What is claimed is:

1. A bypass device for providing fluid channels through a body tissue, the bypass device comprising: an open tubular base; and a plurality of pronged features attached to the open tubular base, the pronged features being reconfigurable from a first position to a second position; wherein in the first position the pronged features extend longitudinally along a plane of the open tubular base, and the pronged features are reconfigurable to the second position by flexing the pronged features relative to the tubular base, such that in the second position the pronged features are configured for insertion through the body tissue, wherein the pronged features are associated in pairs, with individual pronged features of a pair of pronged features being attached to each other via a web, and the pronged features are reconfigurable from the first position to the second position by flexing opposing pronged features of the pair about the web, and wherein individual tangs within a pair of opposing pronged features are offset relative to each other along the longitudinal axis of the open tubular base.

2. The bypass device of claim 1, wherein the pronged features are configured as multiple arrow-shape tangs that are formed within the tubular base.

3. The bypass device of claim 2, wherein each arrow-shaped tang includes a neck that is flexible relative to the tubular base, and an arrow-shape head that is flexible relative to the neck.

4. The bypass device of claim 2, wherein each individual tang includes a tapered edge that runs from the tubular base to an arrow-shaped head of the tang.

5. The bypass device of claim 1, wherein in the second position the pronged features are configured as tent structures.

6. The bypass device of claim 5, wherein opposing ends of the pronged features are oriented at an angle relative to each other upon formation of the tent structures.

7. A method of performing a minimally invasive glaucoma surgery (MIGS) for treating glaucoma comprising the steps of:
providing a bypass device for bypassing a drainage system of an eye including Schlemm's canal, trabecular meshwork, and collector channels, the bypass device comprising:
an open tubular base; and
a plurality of pronged features attached to the open tubular base, the pronged features being reconfigurable from a first position to a second position;
wherein in the first position the pronged features extend longitudinally along a plane of the open tubular base, and the pronged features are reconfigurable to the second position by flexing the pronged features relative to the tubular base, such that in the second position the pronged features are configured for insertion through a body tissue;
forming a guide hole to access a Schlemm's canal at a trabecular meshwork of an eye;
inserting the bypass device through the guide hole and positioning the bypass device within the Schlemm's canal adjacent to the trabecular meshwork;
reconfiguring a portion of the pronged features from the first position to the second position to form one or more tent structures; and
inserting the one or more tent structures of the bypass device into the trabecular meshwork, wherein the one or more tent structures form tent holes through the trabecular meshwork to define fluid flow channels through the trabecular meshwork.

8. The MIGS method of claim 7, further comprising performing a visualization technique to locate clogged portions of the drainage system, wherein the bypass device is aligned relative to the trabecular meshwork such that the one or more tent structures are positioned at or adjacent to respective clogged portions of the trabecular meshwork as determined by the visualization technique.

9. The MIGS method of claim 7, further comprising performing a heat setting process to securely implant the tent structures in the trabecular meshwork.

10. The MIGS method of claim 9, further comprising performing a heat setting process to securely implant the tent structures in the trabecular meshwork, wherein the heat setting process includes a lateral angle heat set to impart side-to-side forces during release of the guide wire to create tissue engagement of the bypass device with the trabecular meshwork.

11. The MIGS method of claim 7, further comprising injecting a viscoelastic substance into the Schlemm's canal to expand the Schlemm's canal to aid inserting the bypass device.

12. The MIGS method of claim 7, further comprising inserting a canaloplasty device having a lumen through the guide hole, introducing one or more substances into the Schlemm's canal through the lumen, and removing the canaloplasty device after inserting the bypass device into the trabecular meshwork.

13. The MIGS method of claim 12, wherein the one or more substances include a guide wire to aid in positioning the bypass device, glaucoma medication, anti-inflammatory agents, and/or antibiotic releasing pellets.

\* \* \* \* \*